United States Patent [19]

Bickel et al.

[11] Patent Number: 5,037,839

[45] Date of Patent: Aug. 6, 1991

[54] PYRIDINE-2,4-AND -2,5-DICARBOXYLIC ACID AMIDES AND MEDICAMENTS BASED ON THESE COMPOUNDS

[75] Inventors: Martin Bickel, Bad Homburg; Dietrich Brocks, Wiesbaden; Harald Burghard, Schmitten; Volkmar Günzler, Marburg-Cappel; Stephan Henke, Bad Soden am Taunus; Hartmut Hanauske-Abel, Dexheim; Jürgen Mohr, Grünstadt; Georg Tschank, Mainz, all of Fed. Rep. of Germany

[73] Assignee: Hoechst Aktiengesellschaft, Frankfurt am Main, Fed. Rep. of Germany

[21] Appl. No.: 434,402

[22] Filed: Nov. 13, 1989

Related U.S. Application Data

[63] Continuation of Ser. No. 153,087, Feb. 8, 1988, abandoned.

[30] Foreign Application Priority Data

Feb. 10, 1987 [DE] Fed. Rep. of Germany ....... 3703959

[51] Int. Cl.$^5$ .................... A61K 31/44; C07D 213/81; C07D 213/82

[52] U.S. Cl. .................................. 514/354; 514/355; 546/316; 546/323

[58] Field of Search ................ 546/316, 323; 514/354, 514/355

[56] References Cited

U.S. PATENT DOCUMENTS 2,852,519 9/1958 Kruse ................................ 546/170

FOREIGN PATENT DOCUMENTS 0057797 8/1982 European Pat. Off. .
0198202 10/1986 European Pat. Off. .
0278908 8/1988 European Pat. Off. .
2803592 3/1979 Fed. Rep. of Germany .

OTHER PUBLICATIONS

Samejima, Yakugaku Zashi, vol. 80, pp. 1706–1712 (1960); Chem. Abstracts, vol. 55, 10439–10440e (1961).

Talma et al., "Reductions of Activated Carbonyl Compounds with Chiral Bridged 1,4-Dihydropyridines. An Investigation of Scope and Structural Effects", Journal of the American Chemical Society, vol. 107, pp. 3981–3997 (1985).

Thunus et al., "Preparation Des Monesters Des Acides Pyridine Dicarboxyliques", Journal De Pharmacie De Belgique, pp. 3–21, 1968.

Dewar et al., "Effect of Structure on the Stability of Nematic Mesophases",: J. Amer. Chem. Soc. 97 (23), pp. 733–741.

Wolfensberger, et al., "Identification of Quinolinic Acid in Rat and Human Brain Tissue", Neuroscience Letters, vol. 41, pp. 247–252 (1983).

Meyer, 19 Chemical Abstracts, 2953–54 (1925).

Ustavshchikov et al., 58 Chemical Abstracts 2431e (1963).

Nesterova et al., 87 Chemical Abstracts 90773c (1977).

Organikum, Organisch Chemisches Grudpraktikum, VEB Deutscher Verlag der Wissenschaften, pp. 255–256 (15th ed., 1976).

A. Hubbuch, Schutzgruppen in der Peptidsynthese (Teil 1): Schutzgruppentaktik, Amino-und Carboxyl-S-chutzgruppen, Kontakte, 3/79, pp. 15 & 19, et seq.

Houben-Weyl, Methoden der Organischen Chemie (Methods of Organic Chemistry), vol. E5, pp. 496–504, 4th Ed., 1985.

J. Org. Chem., vol. 39, No. 8 (1974), p. 1158.

Elke Langhals et al., "Eine einfache neue Synthese der Fusarinsaure und anderer 5-Alkyl-2-pyridincarbonsauren", No. 5, Liebigs Ann. Chem., pp. 930–949 (1982).

*Primary Examiner*—Bernard I. Dentz
*Attorney, Agent, or Firm*—Finnegan, Henderson, Farabow, Garrett and Dunner

[57] ABSTRACT

The invention relates to pyridine-2,4- and -2,5-dicarboxylic acid derivatives of the formula I

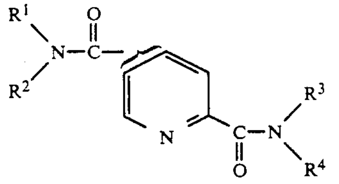

(I)

in which $R^1$, $R^2$, $R^3$, $R^4$ and X have the meanings given, a process for the preparation of these compounds and their use, in particular in medicaments for influencing the metabolism of collagen and collagne-like substances or the biosynthesis of $Cl_q$.

8 Claims, No Drawings

PYRIDINE-2,4-AND -2,5-DICARBOXYLIC ACID AMIDES AND MEDICAMENTS BASED ON THESE COMPOUNDS

This is a continuation of application Ser. No. 07/153,087, filed Feb. 8, 1988 now abandoned.

Compounds which inhibit proline hydroxylase and lysine hydroxylase effect very selective inhibition of collagen biosynthesis by influencing collagen-specific hydroxylation reactions. In the course of these, protein-bonded proline or lysine is hydrolyzed by the enzymes proline hydroxylase and lysine hydroxylase. If this reaction is suppressed by inhibitors, a hypo-hydroxylated collagen molecule which is not capable of functioning and can be released by the cell into the extracellular space in only a small amount is formed. The hypo-hydroxylated collagen also cannot be incorporated into the collagen matrix and is very readily degraded proteolytically. As a consequence of these effects, the total amount of extracellularly deposited collagen is reduced.

It is known that inhibition of proline hydroxylase by known inhibitors, such as $\alpha,\alpha'$-dipyridyl, leads to an inhibition of the $Cl_q$-biosynthesis of macrophages (W. Müller et al., FEBS Lett. 90 (1978), 218; Immunbiology 155 (1978) 47). This results in a loss of the classical route of complement activation. Inhibitors of proline hydroxylase therefore also act as immunosuppressants, for example in immunity complex diseases.

It is known that proline hydroxylase is inhibited effectively by pyridine-2,4- and -2,5-dicarboxylic acid (K. Mayama et al., Eur. J. Biochem. 138 (1984) 239–245). However, these compounds are effective as inhibitors in cell culture only in very high concentrations (V. Günsler et al. Collagen and Rel. Research 3, 71 1983). DE-A 3,432,094 describes pyridine-2,4- and -2,5-dicarboxylic acid diesters with 1-6 carbon atoms in the ester alkyl part as medicaments for inhibiting proline hydroxylase and lysine hydroxylase.

However, these lower alkyl diesters have the disadvantage that they are split too rapidly in the organism to give the acids and do not arrive at their site of action in the cell in a sufficiently high concentration, and therefore are not particularly suitable for possible administration as medicaments.

Surprisingly, it has now been found that the diamides of pyridine-2,4- and -2,5-dicarboxylic acid are excellent inhibitors of collagen biosynthesis in the animal model.

The actual active compound, the pyridine-2,4- or -2,5-dicarboxylic acid, is first formed in the cell by hydrolysis of the diamides. Because of their higher lipophilicity and the fact that, surprisingly, they are hydrolyzed only very slowly during transportation, the diamides can be transported into the cells. Only here is the actual active compound, the pyridine-2,4- or -2,5-dicarboxylic acid, liberated.

The invention thus relates to:

1. Pyridine-2,4- and -2,5-dicarboxylic acid amides of the formula I

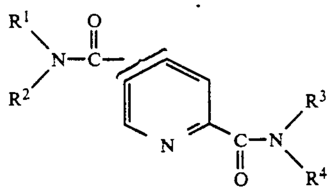

(I)

in which $R^1$ denotes branched or unbranched $C_1$–$C_{12}$-alkyl, which is optionally monosubstituted or, in the case of $C_2$–$C_{12}$-alkyl radicals, also polysubstituted by halogen, hydroxyl, cyano, amino, carboxyl, alkoxy, alkoxycarbonyl, alkylcarbonyloxy or alkyl- or di-alkylamino, wherein the alkyl radicals contain 1–4 carbon atoms and, in the case of the $C_3$- and $C_4$-alkyl radicals, can also be branched, or indolyl or phenyl, which is in turn optionally mono-, di- or trisubstituted by halogen, nitro, $C_1$–$C_4$-alkyl or $C_1$–$C_4$-alkoxy, it also being possible, in the case of polysubstitution, for the substituents to be different independently of one another and, in the case of $C_3$- and $C_4$-alkyl radicals, it also being possible for these to be branched, or $R^1$ denotes saturated $C_5$–$C_7$-cycloalkyl, which is optionally benzo-fused, or $R^1$ denotes aryl or heteroaryl, which is in turn optionally mono-, di- or trisubstituted by halogen, nitro, cyano, $C_1$–$C_4$-alkyl or $C_1$–$C_4$-alkoxy, it also being possible, in the case of polysubstitution, for the substituents to be different independently of one another and, in the case of the $C_3$- and $C_4$-alkyl radicals, it also being possible for these to be branched, and $R^2$, independently of $R^1$ is hydrogen or has one of the meanings described for $R^1$, it also being possible for $R^2$ to be identical to $R^1$, and $R^3$, independently of $R^1$ and $R^2$ is hydrogen or has one of the meanings described for $R^1$, it also being possible for $R^3$ to be identical to $R^1$ and/or $R^2$, and $R^4$, independently of $R^1$, $R^2$ and $R^3$, is hydrogen or has one of the meanings described for $R^1$, it also being possible for $R^4$ to be identical to $R^1$ and/or $R^2$ and/or $R^3$, and in which the radicals $R^1$ and $R^2$ and/or $R^3$ and $R^4$, together with the nitrogen atom, may also form a 5-, 6- or 7-membered saturated heterocyclic ring, it also being possible for the heterocyclic ring to include a second nitrogen atom and it being possible for the heterocyclic ring in turn to be substituted by phenyl or phenyl-$C_1$–$C_3$-alkyl, and physiologically tolerated salts thereof, for use as medicaments, excluding the compounds in which $R^1=R^3$ and these denote phenyl disubstituted by methyl and bromine and $R^2=R^4$ and these denote hydrogen.

The invention particularly relates to pyridine-2,4- and -2,5-dicarboxylic acid amides according to formula I, in which $R^1$ denotes branched or unbranched $C_1$–$C_{12}$-alkyl, which is optionally monosubstituted or, in the case of the $C_3$–$C_{12}$-alkyl radicals, also polysubstituted by amino or $C_1$–$C_3$-alkoxy, it also being possible for the $C_3$-alkyl radicals to be branched, and/or indolyl and/or phenyl, which can be substituted by $C_1$–$C_4$-alkoxy or nitro, or $R^1$ denotes benzo-fused cyclohexyl, or $R^1$ denotes phenyl, which is optionally mono-, di- or trisubstituted by nitro, cyano, halogen or $C_1$–$C_4$-alkyl, it also being possible, in the case of polysubstitution, for the substituents to differ independently of one another, or $R^1$ denotes 2-, 3- or 4-pyridyl, 2- or 3-thienyl or thiazolyl, it also being possible for these heteroatoms to be monosubstituted by $C_1$–$C_4$-alkyl, and $R^2$, independently of $R^1$ is hydrogen or has one of the meanings described for $R^1$, it also being possible for $R^2$ to be identical to $R^1$, and $R^3$, independently of $R^1$ and $R^2$, is hydrogen or has one of the meanings described for $R^1$, it also being possible for $R^3$ to be identical to $R^1$ and/or $R^2$, and $R^4$, independently of $R^1$, $R^2$ and $R^3$, is hydrogen or has one of the meanings described for $R^1$, it also being possible for $R^4$ to be identical to $R^1$ and/or $R^2$ and/or $R^3$, and physiologically tolerated salts thereof, for use as medicaments, excluding the compounds in which $R^1=R^3$ and these denote phenyl which is disubstituted by methyl and bromine and $R^2=R^4$ and these denote hydrogen.

The invention also relates to pyridine-2,4- and -2,5-dicarboxylic acid amides of the formula I'

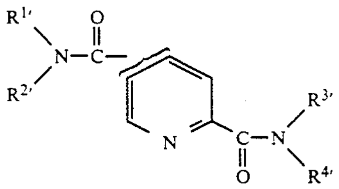

(I')

in which $R^{1'}$ denotes branched or unbranched $C_1$–$C_{12}$-alkyl which is optionally monosubstituted or, in the case of $C_2$–$C_{12}$-alkyl, also polysubstituted by halogen, hydroxyl, cyano, amino, carboxyl, alkoxy, alkoxycarbonyl, alkylcarbonyloxy, alkyl- or dialkylamino, wherein the alkyl radicals contain 1–4 carbon atoms, and it also being possible, in the case of the $C_3$-and $C_4$-alkyl radicals, for these to be branched, or indolyl or phenyl, which is in turn optionally mono-, di or trisubstituted by halogen, nitro, $C_1$–$C_4$-alkoxy or $C_1$–$C_4$-alkyl, it also being possible for the $C_3$- and $C_4$-alkyl radicals mentioned to be branched and it also being possible, in the case of polysubstitution, for the substituents to differ independently of one another, or $R^{1'}$ denotes saturated $C_5$–$C_7$-cycloalkyl, which is optionally benzo-fused, or $R^{1'}$ denotes aryl or heteroaryl, which is in turn optionally mono-, di- or trisubstituted by halogen, nitro, cyano, $C_1$–$C_4$-alkyl or $C_1$–$C_4$-alkoxy, it also being possible, in the case of polysubstitution, for the substituents to differ independently of one another and it also being possible, in the case of the $C_3$- and $C_4$-alkyl radicals, for these to be branched, and $R^{2'}$, independently of $R^{1'}$, is hydrogen or has one of the meanings described for $R^{1'}$, it also being possible for $R^{2'}$ to be identical to $R^{1'}$, $R^{3'}$, independently of $R^{1'}$, is hydrogen or has one of the meanings described for $R^{1'}$, it also being possible for $R^{3'}$ to be identical to $R^{1'}$ and/or $R^{2'}$, and $R^{4'}$, independently of $R^{1'}$, $R^{2'}$ and $R^{3'}$, is hydrogen or has one of the meanings described for $R^{1'}$, it also being possible for $R^{4'}$, to be identical to $R^{1'}$ and/or $R^{2'}$ and/or $R^{3'}$, and in which the radicals $R^{1'}$ and $R^{2'}$ and/or $R^{3'}$ and $R^{4'}$, together with the nitrogen atom, can also form a 5-, 6- or 7-membered saturated heterocyclic ring, it also being possible for the heterocyclic ring to include a second nitrogen atom and it being possible for the heterocyclic ring in turn to be substituted by phenyl or phenyl-$C_1$–$C_3$-alkyl, and physiologically tolerated salts thereof, excluding the compounds in which $R^{1'}=R^{3'}$ and these denote 2-hydroxyethyl or 2-(3,4-dimethoxyphenyl)ethyl or phenyl which is disubstituted by methyl and bromine and $R^{2'}=R^{4'}$ and these denote hydrogen.

Preferred pyridine-2,4- and -2,5-dicarboxylic acid amides according to formula I' are those in which $R^{1'}$ denotes branched or unbranched $C_1$–$C_{12}$-alkyl, which is optionally monosubstituted or, in the case of the $C_2$–$C_{12}$-alkyl radicals, also polysubstituted by amino or $C_1$–$C_3$-alkoxy, it also being possible, in the case of the $C_3$-alkyl compounds, for the alkyl radicals to be branched, or indolyl or phenyl, which can be substituted by $C_1$–$C_4$-alkoxy or nitro, or $R^{1'}$ denotes benzo-fused cyclohexyl, or $R^{1'}$ denotes phenyl, which is optionally substituted by 1, 2 or 3 cyano, halogen, $C_1$–$C_4$-alkyl or nitro groups, it also being possible, in the case of polysubstitution, for the substituents to differ independently of one another, or $R^{1'}$ denotes 2-, 3- or 4-pyridyl, 3-thienyl or thiazolyl, and $R^{2'}$, independently of $R^{1'}$, is hydrogen or has one of the meanings described for $R^{1'}$, it also being possible for $R^{2'}$ to be identical to $R^{1'}$, $R^{3'}$, independently of $R^{1'}$ and $R^{2'}$, is hydrogen or has one of the meanings described for $R^{1'}$, it also being possible for $R^{3'}$ to be identical to $R^{1'}$ and/or $R^{2'}$, and $R^{4'}$, independently of $R^{1'}$, $R^{2'}$ and $R^{3'}$, is hydrogen or has one of the meanings described for $R^{1'}$, it also being possible for $R^{4'}$ to be identical to $R^{1'}$ and/or $R^{2'}$ and/or $R^{3'}$, and physiologically tolerated salts thereof, excluding the compounds in which $R^{1'}=R^{3'}$ and these denote 2-hydroxyethyl or 2-(3,4-dimethoxyphenyl)ethyl or phenyl which is disubstituted by methyl and bromine, and $R^{2'}=R^{4'}$ and these denote hydrogen.

Particularly preferred pyridine-2,4- and -2,5-dicarboxylic acid amides according to formula I' are those as claimed in claim 3, in which $R^{1'}$ denotes branched or unbranched $C_1$–$C_4$-alkyl, which is substituted by $C_1$–$C_3$-alkoxy, it being possible for the alkyl radicals to contain 1–3 carbon atoms and, in the case of the $C_3$-alkyl compounds, also to be branched, and $R^{2'}$, independently of $R^{1'}$, is hydrogen or has one of the meanings described for $R^{1'}$, it also being possible for $R^{2'}$ to be identical to $R^{1'}$, and $R^{3'}$, independently of $R^{1'}$, is hydrogen or has one of the meanings described for $R^{1'}$, it also being possible for $R^{3'}$ to be identical to $R^{1'}$ and/or $R^{2'}$, and $R^{4'}$, independently of $R^{1'}$, $R^{2'}$ and $R^{3'}$, is hydrogen or has one of the meanings described for $R^1$, it also being possible for $R^{4'}$ to be identical to $R^{1'}$ and/or $R^{2'}$ and/or $R^{3'}$, and physiologically tolerated salts thereof.

The last group of compounds mentioned has, inter alia, a particular activity on oral use, as do the especially preferred pyridine-2,4- and -2,5-dicarboxylic acid amides according to formula I' as claimed in claim 3, wherein $R^{1'}$ and $R^{3'}$ are an isopropoxypropyl group and $R^{2'}$ and $R^{4'}$ are hydrogen (such as, for example, pyridine-2,5-dicarboxylic acid N,N'-di(3-isopropoxypropyl)amide, Example 3), pyridine-2,4-dicarboxylic acid bis-3-isopropoxypropylamide (Example 20) and pyridine-2,4- and -2,5-dicarboxylic acid amides according to formula I' as claimed in claim 3, in which $R^{1'}$ and $R^{3'}$ are a 2-methoxy-ethyl group and $R^{2'}$ and $R^{4'}$ are hydrogen, such as, for example, N,N'-bis(2-methoxyethyl)pyridine-2,4-dicarboxylic acid amide (Example 19), and physiologically tolerated salts thereof.

By halogen there are understood fluorine, chlorine, bromine and iodine, by aryl there are understood phenyl and naphthyl, and by heteroaryl there are understood 5-and 6-membered aromatic rings with 1, 2 or 3 nitrogen and/or oxygen and/or sulphur atoms, which can optionally also be benzo-fused; the heteroaryl radicals are, in particular, pyridyl, pyridazyl, pyrimidyl, pyrazyl, 1,3,5-triazyl, pyrolyl, pyrazolyl, imidazolyl, triazolyl, thienyl, oxazolyl and thiazolyl radicals and, where appropriate, benzo-fused compounds thereof.

"Polysubstituted" above and below means that at least 2 and at most all of the hydrogen atoms present in the alkyl radicals are replaced by the substituents mentioned.

It is preferably a case here of one substituent per methyl or methylene group.

In the case of polysubstitution, the substituents can also differ independently of one another.

The invention furthermore relates to a process for the preparation of compounds of the formula I', which comprises reacting a compound of the formula II

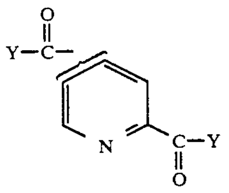

(II)

with a compound of the formula III

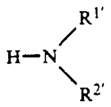

(III)

wherein $R^{1'}=R^{3'}$, $R^{2'}=R^{4'}$ and these have the meanings given in the case of formula I', and Y is halogen or hydroxyl or, together with the carbonyl group, forms an active ester or a mixed anhydride, and, if appropriate, converting the reaction products into their physiologically tolerated salts.

The invention furthermore relates to a process for the preparation of compounds of the formula I', which comprises reacting a compound of the formula II'

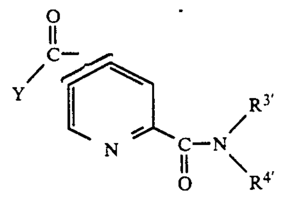

II' with a compound of the formula III

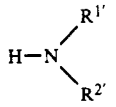

III in which $R^{1'}$, $R^{2'}$, $R^{3'}$ and $R^{4'}$ have the meanings given in the case of formula I' and Y is halogen or hydroxyl or, together with the carbonyl group, forms an active ester or a mixed anhydride, and, if appropriate, converting the reaction products into their physiologically tolerated salts.

The preparation of compounds according to formula I and the preparation of the starting substances required for this—where these are not commercially available—are described in more detail below.

The compounds according to the invention are most easily prepared by mixing the two components, the pyridine derivative according to formula (II) or formula (II') and the amine according to formula (III), in equimolar amounts or with up to about a 5-fold excess of III, and reacting them at temperatures between −30° and 150° C., preferably at 20° to 100° C., until the reaction has ended. The end of the reaction can be determined by means of thin layer chromatography (TLC control). One variant of this process comprises carrying out the reaction in a suitable solvent, such as diethyl ether, dimethoxyethane or tetrahydrofuran, chlorinated hydrocarbons, such as methylene chloride, chloroform or tri- or tetrachloroethylene, benzene, toluene or polar solvents, such as dimethylformamide, acetone or dimethyl sulfoxide. An excess of amine according to formula (III) of up to about 5 times the amount can also be used here. The reaction temperatures here are between room temperature and the boiling point of the solvent, temperatures in the range from room temperature to 130° C. being particularly preferred.

The reaction can likewise take place via a mixed anhydride, such as ethyl chloroformate, or via an activated ester, such as the paranitrophenyl ester ($Y=ClCH_2-COO$ or $NO_2-C_6H_4-O$). Corresponding methods are described in Houben-Weyl, Methoden der Organischen Chemie (Methods of Organic Chemistry), Volume XV/2, pages 169–183 (mixed anhydride method) or pages 13 et seq. (active ester method), fourth edition, Georg Thieme Verlag, Stuttgart 1974.

If appropriate, the reaction can also be carried out in the presence of bases. Possible additional bases are inorganic acid-trapping agents, such as carbonates or bicarbonates, for example sodium carbonate, potassium carbonate, sodium bicarbonate or potassium bicarbonate, or organic acid-trapping agents, such as tertiary amines, such as triethylamine, tributylamine or ethyl diisopropylamine, or heterocyclic amines, such as N-alkylmorpholine, pyridine, quinoline or dialkylanilines.

The reaction of the compounds according to formula (II) or formula (II') with amines according to formula (III) is preferably carried out with the addition of a dehydrating agent, such as a dialkylcarbodiimide, the alkyl radicals containing 1 to 8 C atoms and it also being possible, in the case of the $C_3$–$C_8$-compounds, for the alkyl radicals to be branched or cyclic; dicyclohexylcarbodiimide is preferably used. A corresponding method is described in Houben-Weyl, Volume XV/2, pages 103–111, Methoden der Organischen Chemie (Methods of Organic Chemistry), 4th edition, Georg Thieme Verlag, Stuttgart, 1974.

If appropriate, the products can be worked up, for example, by extraction or by chromatography, for example over silica gel. The isolated product can be recrystallized and if appropriate reacted with a suitable acid to give a physiologically tolerated salt. Examples of possible suitable acids are: mineral acids, such as hydrochloric and hydrobromic acid, as well as sulfuric, phosphoric, nitric or perchloric acid, or organic acids, such as formic, acetic, propionic, succinic, glycolic, lactic, malic, tartaric, citric, maleic, fumaric, phenylacetic, benzoic, methanesulfonic, toluenesulfonic, oxalic, 4-aminobenzoic, naphthalene-1,5-disulfonic or ascorbic acid.

The starting compounds of the formula (III), where they are not commercially available, can be synthesized in a simple manner (for example Organikum, Organisch Chemisches Grundpraktikum (Basic Practical Organic Chemistry), 15th edition, VEB Deutscher Verlag der Wissenschaften, 1976; a review of the various possibilities is to be found in the Method Register, page 822).

The starting compounds of the formula (II) are obtained, for example, by converting pyridine-2,4- or -2,5-dicarboxylic acid into the corresponding pyridine-2,4- or -2,5-dicarboxylic acid halide, preferably chloride (by processes which are known from the literature, for example Organikum, Organisch Chemisches Grundpraktikum (Basic Practical Organic Chemistry), 15th edition, VEB Deutscher Verlag der Wissenschaften, 1976, page 595 et seq.), which is then reacted with a suitable alcohol, for example paranitrobenzyl alcohol, to give the corresponding active ester. The pyridine-2,4- or -2,5-dicarboxylic acid can likewise also first be converted into a mixed anhydride, with the addition of a suitable carboxylic acid or carboxylic acid ester, such as ethyl chloroformate, and the product is then reacted with the amines (III) to give the products according to the invention. A corresponding method is described, for example, in Houben-Weyl, Methoden der organischen Chemie (Methods of Organic Chemistry), Volume XV/2, pages 169–183, fourth edition, 1974, Georg Thieme Verlag Stuttgart.

The starting compounds of the formula (II') can be synthesized, for example, as follows:

Reaction of a pyridine-2,4- or -2,5-dicarboxylic acid halide, preferably the chloride, with benzyl alcohol to give the benzyl pyridine-2,4- or -2,5-dicarboxylate; subsequent selective hydrolysis of the ester in the 2-position (for example in the presence of a copper catalyst, Acta Helv. 44, 1963, page 637), conversion of the free acid in the 2-position into the acid halide, reaction with a compound of the formula (III) to give the pyridine-4- or -5-carboxylic acid benzyl ester-2-carboxylic acid amide, hydrogenolytic splitting off of the benzyl protective group which remains (for example with $H_2$/Pt, see Houben-Weyl Volume IV/1c (1980), pages 381–82), and subsequent conversion of the free acid in the 4- or 5-position of the pyridine ring into the acid halide (II').

The pyridine-2,4- or -2,5-dicarboxylic acid halide can be obtained by known methods, for example by reacting pyridine-2,4- or -2,5-dicarboxylic acid with a phosphorus trihalide (see, for example, Organikum, Organisch Chemisches Grundpraktikum (Basic Practical Organic Chemistry), 15th edition, VEB Deutscher Verlag der Wissenschaften, 1976, pages 527 and 595 et seq.).

The compounds of the formula I and I' according to the invention have valuable pharmacological properties and in particular exhibit an activity as inhibitors of proline hydroxylase and lysine hydroxylase, and as a fibrosuppressant and immunosuppressant.

The activity of the fibrogenase can be determined by radioimmunological assay of the N-terminal propeptide of collagen type III or the N- or C-terminal crosslinking domains of collagen type IV (7s-collagen or type IV collagen-$NC_1$) in the serum.

For this purpose, the hydroxyproline, procollagen-III-peptide, 7s-collagen and type IV collagen-$NC_1$ concentrations in the liver of a) untreated rats (control)

b) rats to which carbon tetrachloride had been administered ($CCl_4$ control)

c) rats to which first $CCl_4$ and then a compound according to the invention had been administered, were measured (this test method is described by Rouiller, C., Experimental toxic injury of the liver; in The Liver, C. Rouiller, Volume 2, pages 335–476, New York, Academic Press, 1964).

The pharmacological activity of the substances according to the invention was investigated in two series of experiments (see Tables 1 and 2). A clear inhibition of proline hydroxylase and lysine hydroxylase was found here.

TABLE 1

| Substance from Example | Dosage | Hydroxyproline μg/mg of liver | Procollagen III peptide ng/ml | 7s-collagen ng/ml | Type I collagen $NC_1$ ng |
|---|---|---|---|---|---|
| 2 | | 0.407 | 56.9 | 217.1 | 110.9 |
| CCl4 control | | 0.733 | 81.5 | 477.5 | 192.1 |
| control | | 0.143 | 21.4 | 29.1 | 24.9 |

TABLE 2

| Substance from Example | Dosage | Hydroxyproline μg/mg of liver | Procollagen III peptide ng/ml | 7s-collagen ng/ml | Type I collagen $NC_1$ ng |
|---|---|---|---|---|---|
| 3 | 2 × 25 mg | 0.534 | 48.5 | 278.1 | 181.4 |
| CCl4 control | | 0.773 | 73.9 | 308.7 | 168.4 |

TABLE 2-continued

| Substance from Example | Dosage | Hydroxyproline μg/mg of liver | Procollagen III peptide ng/ml | 7s-collagen ng/ml | Type I collagen $NC_1$ ng |
|---|---|---|---|---|---|
| control | | 0.289 | 11.1 | 22.8 | 23.5 |

The compounds of the formula I and I' can be used as medicaments in the form of pharmaceutical preparations which contain them, if appropriate together with tolerated pharmaceutical excipients. The compounds can be used as medicines, for example in the form of pharmaceutical preparations containing these compounds as a mixture with a pharmaceutical organic or inorganic excipient suitable for enteral, percutaneous or parenteral administration, such as, for example, water, gum arabic, gelatin, lactose, starch, magnesium stearate, talc, vegetable oils, polyalkylene glycols, white petroleum jelly and the like.

The pharmaceutical preparations can be in the solid form, for example as tablets, coated tablets, suppositories or capsules; in the semi-solid form, for example as ointments, or in the liquid form, for example as solutions, suspensions or emulsions. If appropriate, they are sterilized and/or contain auxiliaries, such as preservatives, stabilizers, wetting agents or emulsifying agents, salts for modifying the osmotic pressure or buffers. They can furthermore also contain other therapeutically active substances.

The invention is illustrated in more detail with the aid of examples below:

EXAMPLES

1. Pyridine-2,5-dicarboxylic acid N,N'-diethylamide 100 g of pyridine-2,5-dicarboxylic acid are taken in 600 ml of dry methylene chloride, and 800 ml of freshly distilled thionyl chloride and 4 ml of dry dimethylformamide are added. The mixture is boiled under reflux for three hours, the excess thionyl chloride and the methylene chloride are then distilled off and the residue is evaporated, with fuming, once with dry toluene. A solution of 108 g of ethylamine dissolved in 1,000 ml of methylene chloride is added dropwise to the reaction mixture at −30° to −20° C. The mixture is allowed to warm slowly to room temperature and is stirred overnight at room temperature, and the product which has precipitated out is filtered off. The mother liquor is washed with sodium bicarbonate solution and, after drying, the organic phase is freed from the solvent. The combined products are recrystallized from ethyl acetate.

Melting point 182° C.: Yield 114 g.

2. Pyridine-2,4-dicarboxylic acid N,N'-diethylamide 100 g of pyridine-2,4-dicarboxylic acid are reacted analogously to Example 1 and the product is worked up accordingly.

Melting point 117° C.: Yield 135 g.

3. Pyridine-2,5-dicarboxylic acid N,N'-di(3-isopropoxypropyl)amide 10 g of pyridine-2,5-dicarboxylic acid are taken in 60 ml of dry methylene chloride, and 80 ml of freshly distilled thionyl chloride and 2 ml of dry dimethylformamide are added. The mixture is boiled under reflux for three hours, the excess thionyl chloride and the methylene chloride are then distilled off and the residue is evaporated, with fuming, once with dry toluene. A solution of 17.5 g of 3-isopropoxypropylamine, dissolved in 200 ml of methylene chloride, is added dropwise to the reaction mixture at −30° to −20° C. The mixture is allowed to warm slowly to room temperature and is stirred overnight at room temperature, the reaction mixture is washed with sodium bicarbonate solution and, after drying, the organic phase is freed from the solvent. The product is chromatographed over silica gel.

Melting point 92° C.: Yield 8.5 g.

4. Pyridine-2,5-dicarboxylic acid N,N'-di(1,2,3,4-tetrahydronaphth-1-yl)amide 10 g of pyridine-2,5-dicarboxylic acid are converted into the acid chloride in accordance with Example 3 and this is then reacted with 22.0 g of 1,2,3,4-tetrahydro-1-naphthylamine. For purification, the product is boiled up with ethanol.

Melting point 206° C.: Yield 14.8 g.

5. Pyridine-2,5-dicarboxylic acid N,N'-dibenzylamide 10 g of pyridine-2,5-dicarboxylic acid are first converted into the acid chloride in accordance with Example 3 and this is then reacted with 16.04 g of benzylamide. For purification, the product is washed with bicarbonate solution, chromatographed over silica gel and then recrystallized from ethanol.

Melting point 188°-89° C.: Yield 2.5 g.

6. Pyridine-2,5-dicarboxylic acid N,N'-diisopropylamide 10 g of pyridine-2,5-dicarboxylic acid are converted into the acid chloride in accordance with Example 3 and this is then reacted with 8.85 g of anhydrous isopropylamine. For purification, the product is washed with bicarbonate solution, chromatographed over silica gel and recrystallized from ethanol.

Melting point 175°-6° C.: Yield 3.9 g.

7. Pyridine-2,5-dicarboxylic acid N,N'-dipyrid-2-ylamide 10 g of pyridine-2,5-dicarboxylic acid are converted into the acid chloride in accordance with Example 3 and this is then reacted with 14.1 g of 2-aminopyridine. For purification, the product is washed with bicarbonate solution, chromatographed over silica gel and recrystallized from ethanol.

Melting point 216°-17° C.: Yield 2.4 g.

8. Pyridine-2,5-dicarboxylic acid N,N'-di(3-phenylpropyl)amide 10 g of pyridine-2,5-dicarboxylic acid are converted into the acid chloride in accordance with Example 3 and this is then reacted with 17 g of 3-phenylpropylamine. For purification, the product is recrystallized from ethanol.

Melting point 139° C.: Yield 13.6 g.

9. Pyridine-2,5-dicarboxylic acid N,N'-di(1-methoxyprop-2-yl)amide 10 g of pyridine-2,5-dicarboxylic acid are converted into the acid chloride in accordance with Example 3 and this is then reacted with 10.7 g of 2-amino-1-methoxy-propane. For purification, the product is chromatographed over silica gel with ethyl acetate.

Melting point 112°-113° C.: Yield 6.4 g.

10. Pyridine-2,5-dicarboxylic acid N,N'-di(2-methoxyethyl)amide 10 g of pyridine-2,5-dicarboxylic acid are converted into the acid chloride in accordance with Example 3 and this is then reacted with 9 g of 2-methoxy-ethylamine. For purification, the product is chromatographed over silica gel with a mixture of methylene chloride and acetone.

Melting point 97° C.: Yield 2.2 g.

11. Pyridine-2,5-dicarboxylic acid N,N'-di(thiazol-2-yl)amide 1.02 g of di(4-nitrophenyl) pyridine-2,4,5-dicarboxylate are dissolved in 30 ml of dry dimethylformamide and reacted with 0.5 g of 2-aminothiazole and 0.45 ml of triethylamine at room temperature for three hours. The reaction mixture is taken up in diethyl ether and washed several times with water. The aqueous phase is extracted once with ethyl acetate and the organic phases are combined, dried and chromatographed over silica gel with a 4:1 mixture of toluene and ethyl acetate.

Melting point 249° C.: Yield 0.176 g.

12.

N,N'-Bis(3-dibutylamino-propyl)-pyridine-2,5-dicarboxylic acid amide 5 g of pyridine-2,5-dicarboxylic acid are converted into the acid chloride in accordance with Example 3 and this is reacted with 11.2 g of N,N'-dibutyl-1,3-propanediamine in methylene chloride. The reaction mixture is stirred with sodium bicarbonate solution, the phases are separated and the aqueous phase is extracted with methylene chloride. The combined organic phases are dried and freed from the solvent. The product is taken up in acetone and oxalic acid is added. The oxalate formed is re-crystallized first from ethyl acetate-methanol and a second time from isopropanol-acetone.

Melting point 139° C.: Yield 8.2 g.

13.

N,N'-Bis(2-(2-methoxyphenyl)ethyl)-pyridine-2,5-dicarboxylic acid amide 5 g of pyridine-2,5-dicarboxylic acid are converted into the acid chloride in accordance with Example 3 and this is reacted with 9.1 g of 2-(2-methoxyphenyl)ethylamine in methylene chloride. The reaction mixture is stirred with sodium bicarbonate solution, the phases are separated and the aqueous phase is extracted with methylene chloride. The combined organic phases are dried and freed from the solvent. The product is recrystallized twice from ethyl acetate and washed with diethyl ether.

Melting point 139°-40° C.: Yield 2.5 g.

14.

N,N'-Bis(4-methyl-thien-3-yl)-pyridine-2,5-dicarboxylic acid amide 5 g of pyridine-2,5-dicarboxylic acid are converted into the acid chloride in accordance with Example 3 and this is reacted with 6.8 g of 3-amino-4-methylthiophene in methylene chloride. The reaction mixture is stirred with sodium bicarbonate solution, the phases are separated and the aqueous phase is extracted with methylene chloride. The combined organic phases are dried and freed from the solvent. The product is recrystallized twice from ethyl acetatemethanol.

Melting point 209° C.: Yield 3.0 g.

15.

N,N'-Bis(2-indol-3-yl)prop-2-yl)-pyridine-2,5-dicarboxylic acid amide 5 g of pyridine-2,5-dicarboxylic acid are converted into the acid chloride in accordance with Example 3 and this is reacted with 10.4 g of α,α-dimethyltryptamine in methylene chloride. The reaction mixture is stirred with sodium bicarbonate solution, the phases are separated and the aqueous phase is extracted with methylene chloride. The combined organic phases are dried and freed from the solvent.

Melting point 129°-30° C.: Yield 1.0 g.

16. N,N'-Bis(dodecyl)-pyridine-2,5-dicarboxylic acid amide 5 g of pyridine-2,5-dicarboxylic acid are converted into the acid chloride in accordance with Example 3 and this is reacted with 11.1 g of dodecylamine in methylene chloride. The reaction mixture is stirred with sodium bicarbonate solution, the phases are separated and the aqueous phase is extracted with methylene chloride. The combined organic phases are dried and freed from the solvent.

Melting point 122° C.: Yield 3.8 g.

17.

N,N'-Bis(2-(4-nitrophenyl)ethyl)-pyridine-2,5-dicarboxylic acid amide 2 g of di(4-nitrophenyl) pyridine-2,5-dicarboxylate are taken in 60 ml of dimethylformamide, 4 ml of triethylamine and 1.98 g of 2-(4-nitrophenyl)ethylamine are added and the mixture is stirred at room temperature for three hours. Ethyl acetate is added and the reaction mixture is washed several times with water and with sodium bicarbonate solution. The organic phase is dried and freed from the solvent. The product is recrystallized twice from ethyl acetate and washed with diethyl ether.

Melting point 211°-12° C.: Yield 1.1 g.

18. N,N'-Bis(2-cyanophenyl)pyridine-2,5-dicarboxylic acid amide 5 g of pyridine-2,5-dicarboxylic acid are converted into the acid chloride in accordance with Example 3 and this is reacted with 7.1 g of 2-aminobenzonitrile in methylene chloride. The reaction mixture is stirred with sodium bicarbonate solution, the phases are separated and the aqueous phase is extracted with methylene chloride. The combined organic phases are dried and freed from the solvent. The residue is stirred with diethyl ether, filtered off with suction, boiled up with ethyl acetate/methanol, cooled, filtered off with suction and washed with diethyl ether.

Melting point 252° C.: Yield 1.67 g.

19. N,N'-Bis(2-methoxy-ethyl)-pyridine-2,4-dicarboxylic acid amide 10 g of pyridine-2,4-dicarboxylic acid are converted into the acid chloride in accordance with Example 3 and this is reacted with 8.98 g of 2-methoxyethylamine in methylene chloride. The reaction mixture is stirred with sodium bicarbonate solution and the organic phase is separated off, dried and freed from the solvent. The residue is chromatographed over silica gel with a 3:1 mixture of ethyl acetate and methanol. The resulting oil is stirred with ethyl acetate/petroleum ether and, after crystallization, the crystals are filtered off with suction.

Melting point 86° C.: Yield 0.8 g.

20. Pyridine-2,4-dicarboxylic acid bis-3-isopropoxypropylamide 10 g of pyridine-2,4-dicarboxylic acid are taken in 60 ml of dry methylene chloride, and 80 ml of freshly distilled thionyl chloride and 2 ml of dry dimethylformamide are added. The mixture is boiled under reflux for three hours, the excess thionyl chloride and the methylene chloride are then distilled off and the residue is evaporated, with fuming, once with dry toluene. A solution of 17.5 g of 3-isopropoxypropylamine, dissolved in 200 ml of methylene chloride, is added dropwise to the reaction mixture at −30° to −20° C. The mixture is allowed to warm slowly to room temperature and is stirred overnight at room temperature, the reaction mixture is washed with sodium bicarbonate solution and, after drying, the organic base is freed from the solvent. The product is chromatographed over silica gel.

Melting point 49° C.: Yield 12.9 g.

21. Pyridine-2-(3-isopropoxypropyl)carboxylic acid amide-5-(3-(N,N-dibutylamino)propyl)carboxylic acid amide 1 g of pyridine-5-carboxylic acid-2-(3-isopropoxypropyl)-carboxylic acid amide is boiled under reflux in 20 ml of thionyl chloride until a clear solution has formed. The mixture is left to stand at room temperature for one hour, the thionyl chloride is distilled off and 0.7 g of N,N-dibutyl-1,3-propanediamine in 30 ml of methylene chloride are added dropwise. The reaction mixture is stirred at room temperature for 30 minutes and freed from the solvent and the residue is chromatographed over silica gel with a 1:1 mixture of ethyl acetate and methanol.

Yield 0.22 g: oil.

We claim:

1. A pyridine-2,4- or -2,5-dicarboxylic acid amide of the formula I'

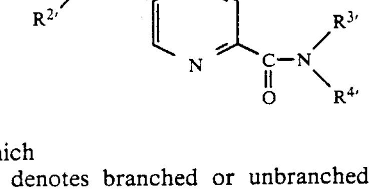

(I')

in which $R^{1'}$ denotes branched or unbranched $C_1$–$C_4$-alkyl, which is substituted by $C_1$–$C_3$-alkoxy, it being possible for the $C_3$-alkyl moiety of the $C_3$-alkoxy group to be branched, and $R^{2'}$, independently of $R^{1'}$, is hydrogen or has one of the meanings described for $R^{1'}$, it also being possible for $R^{2'}$ to be identical to $R^{1'}$ and $R^{3'}$, independently of $R^{1'}$, is hydrogen or has one of the meanings described for $R^{1'}$, it also being possible for $R^{3'}$ to be identical to $R^{1'}$ and/or $R^{2'}$, and $R^{4'}$ independently of $R^{1'}$, $R^{2'}$ and $R^{3'}$ is hydrogen or has one of the meanings described for $R^{1'}$, it also being possible for $R^{4'}$ to be identical to $R^{1'}$ and/or $R^{2'}$ and/or $R^{3'}$ or a physiologically tolerated salt thereof.

2. A pyridine-2,4- or -2,5-dicarboxylic acid amide of the formula I'

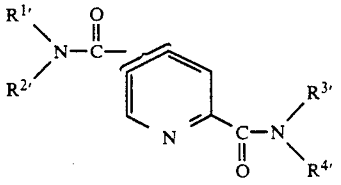

(I')

in which $R^{1'}$ denotes a 3-isopropoxypropyl group;

$R^{2'}$ denotes hydrogen;

$R^{3'}$ denotes a 3-isopropoxypropyl group; and $R^{4'}$ denotes hydrogen;

or a physiologically tolerated salt thereof.

3. A pyridine-2,4- or -2,5-dicarboxylic acid amide of the formula I'

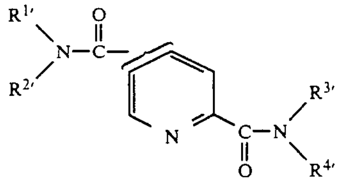

(I')

in which $R^{1'}$ denotes a 2-methoxyethyl group;

$R^{2'}$ denotes hydrogen;

$R^{3'}$ denotes a 2-methoxyethyl group; and $R^{4'}$ denotes hydrogen;

or a physiologically tolerated salt thereof.

4. A method for inhibiting proline hydroxylase and lysine hydroxylase in a mammal comprising administering a pharmaceutically effective amount of a compound of the formula I' as claimed in claim 1.

5. A method for fibrosuppression and immunosuppression in a mammal comprising administering a pharmaceutically effective amount of a compound of the formula I' as claimed in claim 1.

6. A method for influencing the metabolism of collagen and collagen-like substances or the biosynthesis of Clq in a mammal comprising administering a pharmaceutically effective amount of a compound of the formula I' as claimed in claim 1.

7. A method for treating a disturbance of the metabolism of collagen and collagen-like substances or the biosynthesis of Clq in a mammal comprising administering a pharmaceutically effective amount of a compound of the formula I' as claimed in claim 1.

8. A pharmaceutical composition for the inhibition of proline and lysine hydroxylase in a mammal which comprises an effective amount for said inhibition of a compound of the formula I' as claimed in claim 17 together with a pharmaceutically tolerated vehicle.

* * * * *